(12) United States Patent
Brown et al.

(10) Patent No.: US 9,082,596 B2
(45) Date of Patent: Jul. 14, 2015

(54) METHOD OF SINGLE POINT INTERNAL LOCK-MOBILITY CORRECTION

(75) Inventors: Jeffery Mark Brown, Hyde (GB); Kevin Giles, Stockport (GB)

(73) Assignee: Micromass UK Limited, Wilmslow (GB)

(*) Notice: Subject to any disclaimer, the term of this patent is extended or adjusted under 35 U.S.C. 154(b) by 34 days.

(21) Appl. No.: 14/123,532

(22) PCT Filed: Jun. 1, 2012

(86) PCT No.: PCT/GB2012/051250
§ 371 (c)(1),
(2), (4) Date: Mar. 19, 2014

(87) PCT Pub. No.: WO2012/164306
PCT Pub. Date: Dec. 6, 2012

(65) Prior Publication Data
US 2015/0090873 A1    Apr. 2, 2015

Related U.S. Application Data

(60) Provisional application No. 61/497,307, filed on Jun. 15, 2011.

(30) Foreign Application Priority Data

Jun. 3, 2011    (GB) .................................. 1109416.6

(51) Int. Cl.
*H01J 49/40*    (2006.01)
*H01J 49/02*    (2006.01)
(Continued)

(52) U.S. Cl.
CPC .......... *H01J 49/0031* (2013.01); *G01N 27/622* (2013.01); *H01J 49/26* (2013.01)

(58) Field of Classification Search
CPC .............. H01J 49/0009; H01J 49/0027; H01J 49/0031; H01J 49/0036; H01J 49/34; H01J 49/36; H01J 49/40; H01J 49/401; H01J 49/402; H01J 49/42
USPC .................................. 250/281, 282, 286, 287
See application file for complete search history.

(56) References Cited

U.S. PATENT DOCUMENTS 5,796,099 A *   8/1998   Jackson ......................... 250/286
7,751,999 B1 *  7/2010   McAtee et al. ................. 702/85

(Continued)

OTHER PUBLICATIONS

Williams et al, "Characterization of Simple Isomeric Oligosaccharides and the Rapid Separation of Glycan Mixtures by Ion Mobility Mass Spectrometry", International Journal of Mass Spectrometry 298 (2010), 119-127.*

(Continued)

*Primary Examiner* — Jack Berman
*Assistant Examiner* — David E Smith
(74) *Attorney, Agent, or Firm* — Diederiks & Whitelaw, PLC

(57) ABSTRACT

A method of mass spectrometry is disclosed comprising passing ions through an ion mobility spectrometer and acquiring first ion mobility drift time data. A calibration function is applied to the first ion mobility drift time data to determine a physico-chemical property (e.g. CCS) of the ions. Second ion mobility drift time data is then acquired and the calibration function is applied to the second ion mobility drift time data to determine the physico-chemical property of one or more known or reference ions. The calibration function is then adjusted.

12 Claims, 12 Drawing Sheets

(51) Int. Cl.
  *H01J 49/00* (2006.01)
  *G01N 27/62* (2006.01)
  *H01J 49/26* (2006.01)

(56) References Cited

U.S. PATENT DOCUMENTS

2005/0253061 A1* 11/2005 Cameron et al. ............ 250/287
2010/0200742 A1   8/2010 Schultz et al.
2014/0051181 A1   2/2014 Brown et al.

OTHER PUBLICATIONS

Thalassinos et al, "Characterization of Phosphorylated Peptides Using Traveling Wave-Based and Drift Cell Ion Mobility Mass Spectrometry", Anal. Chem. 2009, 81, 248-254.*

Bush et al., "Collision Cross Sections of Proteins and Their Complexes: A Calibration Framework and Database for Gas-Phase Structural Biology", Analytical Chemistry, vol. 82, No. 22, pp. 9557-9565.

Ruotolo et al., "Gas-Phase Conformations of Proteolytically Derived Protein Fragments: Influence of Solvent on Peptide Conformation", The Journal of Physical Chemistry, vol. 108, No. 39, pp. 15321-15331.

Thalassinos et al., "Characterization of Phosphorylated Peptides Using Traveling Wave-Based and Drift Cell Ion Mobility Mass Spectrometry", Analytical Chemistry, vol. 81, No. 1, pp. 248-254.

Williams et al., "Characterization of Simple Isomeric Oligosaccharides and the Rapid Separation of Glycan Mixtures by Ion Mobility Mass Spectrometry", International Journal of Mass Spectrometry, vol. 298, No. 1-3, pp. 119-127.

* cited by examiner

Fig. 3

| CCS(Å$^2$) | RISELR | RLSELR | Ac-RISELR | Ac-RLSELR |
|---|---|---|---|---|
| c2 | 106.2 | 106.29 | 115.02 | 115.72 |
| c3 | 121.84 | 122.77 | 129.9 | 130.99 |
| c4 | 144.34 | 143.89 | 146.06 | 147.82 |
| c5 | 166.05 | 165.86 | 169.68 | 171.07 |
| z2 | - | - | - | - |
| z3 | 128.12 | 127.98 | 128.35 | 127.56 |
| z4 | 144.02 | 143.73 | 144.27 | 143.46 |
| z5 | 166.54 | 166.68 | 166.68 | 166.49 |
| [M+H]$^+$ | 193.79 | 194.06 | 197.06 | 198.98 |
| [M+2H]$^{+\cdot}$ | 194.03 | 194.81 | 201.47 | 201.36 |
| ΔCCS(%) | 0.12 | 0.38 | 2.19 | 1.18 |
| [M+2H]$^{2+}$ | 207.01 | 210.8 | 214.3 | 216.53 |

| CCS(Å$^2$) | HISELR | HLSELR | Ac-HISELR | Ac-HLSELR |
|---|---|---|---|---|
| c2 | - | - | - | - |
| c3 | 117.7 | 120.38 | - | - |
| c4 | 139.89 | 141.35 | - | - |
| c5 | 161.86 | 163.16 | 167.93 | 169.7 |
| z2 | 106.93 | 106.74 | - | - |
| z3 | 127.64 | 127.73 | 128.07 | 127.81 |
| z4 | 143.87 | 143.57 | 143.99 | 143.68 |
| z5 | 166.14 | 166.32 | 166.27 | 166.49 |
| [M+H]$^+$ | 190.21 | 191.14 | 200.16 | 200.4 |
| [M+2H]$^{+\cdot}$ | 190.92 | 191.79 | 200.14 | 200.31 |
| ΔCCS(%) | 0.37 | 0.34 | -0.01 | -0.04 |
| [M+2H]$^{2+}$ | 212.3 | 212.3 | 217.35 | 217.35 |

Fig. 9

| CCS(Å$^2$) | KISELR | KLSELR | Ac-KISELR | Ac-KLSELR |
|---|---|---|---|---|
| c2 | - | - | - | - |
| c3 | 116.55 | 117.55 | - | - |
| c4 | 138.02 | 139.45 | - | - |
| c5 | 162.26 | 163.31 | 168.55 | 169.89 |
| z2 | 106.48 | 106.71 | - | - |
| z3 | 127.89 | 127.92 | 127.91 | 128.03 |
| z4 | 143.81 | 143.82 | 143.87 | 143.92 |
| z5 | 166.06 | 166.51 | 166.2 | 166.75 |
| [M+H]$^+$ | 189.16 | 189.89 | 198.29 | 198.24 |
| [M+2H]$^{+\cdot}$ | 190.34 | 191.43 | 198.92 | 199.53 |
| ΔCCS(%) | 0.62 | 0.80 | 0.32 | 0.65 |
| [M+2H]$^{2+}$ | 204.07 | 204.6 | 206.75 | 206.67 |

Fig. 11

| | RISDLR | RLSDLR | Ac-RISDLR | Ac-RLSDLR | KISDLR | KLSDLR | Ac-KISDLR | Ac-KLSDLR |
|---|---|---|---|---|---|---|---|---|
| c2 | 106.29 | 106.56 | 115.22 | 116.28 | - | - | - | - |
| c3 | 121.42 | 122.66 | 129.68 | 131.02 | - | - | - | - |
| c4 | 141.49 | 142.19 | 144.72 | 146.04 | 135.2 | 136.8 | - | - |
| c5 | 162.18 | 162.56 | 167.88 | 169.77 | 158.15 | 159.8 | - | - |
| z2 | - | - | - | - | 107.91 | 108.28 | 124.28 | 124.37 |
| z3 | 123.89 | - | - | - | 124.08 | 124.07 | - | - |
| z4 | 140.33 | 140.14 | 140.42 | 140.18 | 140.33 | 140.24 | 140.17 | 140.13 |
| z5 | 163.26 | 164.23 | 163.35 | 164.17 | 163.28 | 164.06 | 163.06 | 163.84 |
| $[M+H]^+$ | 188.45 | 188.83 | 193.76 | 195.56 | 186.17 | 186.55 | 189.17 | 191.37 |
| $[M+2H]^{+\cdot}$ | 194.31 | 195.45 | 199.49 | 199.99 | 188.28 | 189.19 | 195.88 | 196.3 |
| ΔCCS(%) | 3.02 | 3.39 | 2.87 | 2.22 | 1.12 | 1.40 | 3.43 | 2.51 |
| $[M+2H]^{2+}$ | 213.37 | 213.36 | 213.78 | 216.06 | 203.33 | 204.11 | 203.94 | 206.26 | great pains
METHOD OF SINGLE POINT INTERNAL LOCK-MOBILITY CORRECTION

CROSS REFERENCE TO RELATED APPLICATIONS

This application is the National Stage of International Application No. PCT/GB2012/051250, filed 1 Jun. 2012, which claims priority from and the benefit of U.S. Provisional Patent Application Ser. No. 61/497,307 filed on 15 Jun. 2011 and United Kingdom Patent Application No. 1109416.6 filed on 3 Jun. 2011. The entire contents of these applications are incorporated herein by reference.

BACKGROUND OF THE INVENTION

The present invention relates to a method of mass spectrometry and a mass spectrometer. The preferred embodiment relates an improved method of calibrating ion mobility drift times which enables detailed studies of Electron Transfer Dissociation ('ETD') fragment ion structures using ion mobility mass spectrometry to be performed.

Ion mobility is a powerful technique for obtaining structural information for ions ranging from peptide fragments to large protein complexes. Certain secondary structures such as helices are known to have larger collision cross sections ("CCS") than predicted values. Intramolecular interactions such as salt-bridges or charge solvation by backbone amide groups can cause conformation contractions leading to experimental collision cross sections which are smaller than predicted. N-terminal acetylation and a basic C terminal residue (His, Arg, Lys) may stabilize the secondary structure.

The study of Electron Transfer Dissociation ("ETD") fragment ion structures using ion mobility mass spectrometry can be used to determine how charge-carrying amino acid residues affect the structure of solvent-free peptide cations and of radical cations. ETD may also be used to establish the effect of N-terminal acetylation on the structure of peptides containing amino acid side chains prone to form intramolecular interactions.

In order to perform detailed studies of ETD fragment ion structures it is necessary to make accurate measurements of the ion mobility drift times of ETD fragment ions and to correlate the measured ion mobility drift time with a collision cross section ("CCS") of the ions.

It is known to use either a multi-point external calibration or a multi-point internal calibration method to determine a calibration function which relates the experimentally determined ion mobility drift time with a collision cross section ("CCS").

The known techniques determine a calibration function which is then used during a subsequent ion mobility experiment.

However, during the course of an ion mobility experiment there may be a slight change in one or more instrument parameters (e.g. temperature, pressure etc.) and these can affect the measured ion mobility drift time during the ion mobility experiment.

As a result, current techniques do not enable very detailed ion mobility experiments to be performed which seek to understand very precise or small conformational changes in e.g. the structure of peptides having slightly different sequences.

It is desired to provide an improved mass spectrometer and method of mass spectrometry.

SUMMARY OF THE PRESENT INVENTION

According to an aspect of the present invention there is provided a method of mass spectrometry comprising:

separating a first plurality of ions including one or more known or reference ions according to their ion mobility and acquiring first ion mobility data;

applying an initial calibration function to the first ion mobility data;

determining an estimated property of the one or more known or reference ions;

comparing the estimated property with a known property of the one or more known or reference ions; and varying the initial calibration function to generate a revised calibration function.

The method preferably further comprises determining the initial calibration function using a multi-point external calibration method.

The method may further comprise determining the initial calibration function using a multi-point internal calibration method.

The initial calibration function preferably relates experimentally determined ion mobility drift times of ions with a physico-chemical property of the ions.

The physico-chemical property preferably comprises a conformational property of the ions.

The conformational property preferably comprises a collision cross section ("CCS") of the ions.

The estimated property and/or the known property preferably comprises a collision cross section ("CSS") of the ions.

The step of varying the initial calibration function preferably comprises altering one or more constants in the initial calibration function.

The step of varying the initial calibration function preferably comprises altering a first order coefficient and/or a first order term in the initial calibration function.

The step of varying the initial calibration function may comprise altering a second or higher order coefficient and/or a second or higher order term in the initial calibration function.

The step of varying the initial calibration function preferably comprises altering one or more constants and/or one or more coefficients and/or one or more terms of the initial calibration function to generate the revised calibration function.

According to an embodiment an estimated property of the one or more known or reference ions as determined using the revised calibration function corresponds more closely with the known property of the one or more known or reference ions than an estimated property of the one or more known or reference ions as determined using the initial calibration function.

The step of varying the initial calibration function is preferably performed in real-time during an experimental acquisition.

The method preferably further comprises:

separating a second plurality of ions according to their ion mobility and acquiring second ion mobility data;

applying the revised calibration function to the second ion mobility data; and determining the estimated property of the second plurality of ions.

According to a less preferred embodiment the step of varying the initial calibration function may be performed after an experimental acquisition as a post-processing step.

The one or more known or reference ions preferably comprise one or more parent or precursor ions.

The one or more known or reference ions preferably comprise one or more fragment, daughter or product ions.

According to an aspect of the present invention there is provided a mass spectrometer comprising:

an ion mobility spectrometer or separator arranged and adapted to separate a first plurality of ions including one or more known or reference ions according to their ion mobility; and a control system arranged and adapted:

(i) to acquire first ion mobility data;

(ii) to apply an initial calibration function to the first ion mobility data;

(iii) to determine an estimated property of the one or more known or reference ions;

(iv) to compare the estimated property with a known property of the one or more known or reference ions; and (v) to vary the initial calibration function to generate a revised calibration function.

According to an aspect of the present invention there is provided a method of mass spectrometry comprising:

determining an initial calibration function which correlates experimentally determined ion mobility drift times of ions with collision cross sections ("CSS") of the ions;

separating a first plurality of ions including one or more known or reference ions according to their ion mobility and acquiring first ion mobility drift time data;

applying the initial calibration function to the first ion mobility drift time data;

determining a first collision cross section of the one or more known or reference ions using the initial calibration function;

comparing the first collision cross section as determined using the initial calibration function with a known collision cross section of the one or more known or reference ions;

varying the initial calibration function to generate a revised calibration function, wherein a collision cross section of the one or more known or reference ions determined using the revised calibration function correlates more closely with the known collision cross section than the first collision cross section;

separating a second plurality of ions according to their ion mobility and acquiring second ion mobility drift time data;

applying the revised calibration function to the second ion mobility drift time data; and determining a collision cross section of the second ions using the revised calibration function.

According to an aspect of the present invention there is provided a mass spectrometer comprising:

an ion mobility spectrometer or separator arranged and adapted to separate ions according to their ion mobility; and a control system arranged and adapted:

(i) to determine an initial calibration function which correlates experimentally determined ion mobility drift times of ions with collision cross sections ("CSS") of the ions;

(ii) to cause a first plurality of ions including one or more known or reference ions to be separated according to their ion mobility in the ion mobility spectrometer or separator and to acquire first ion mobility drift time data;

(iii) to apply the initial calibration function to the first ion mobility drift time data;

(iv) to determine a first collision cross section of the one or more known or reference ions using the initial calibration function;

(v) to compare the first collision cross section as determined using the initial calibration function with a known collision cross section of the one or more known or reference ions;

(vi) to vary the initial calibration function to generate a revised calibration function, wherein a collision cross section of the one or more known or reference ions determined using the revised calibration function correlates more closely with the known collision cross section than the first collision cross section;

(vii) to cause a second plurality of ions to be separated according to their ion mobility in the ion mobility spectrometer or separator and to acquire second ion mobility drift time data;

(viii) to apply the revised calibration function to the second ion mobility drift time data; and (ix) to determine a collision cross section of the second ions using the revised calibration function.

According to an embodiment the mass spectrometer may further comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive on source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; and (xx) a Glow Discharge ("GD") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic or orbitrap mass analyser, (x) a Fourier Transform electrostatic or orbitrap mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (ill) a Paul or 3D quadrupole ion trap; (iv) a Penning ion trap; (v) an ion trap; (vi) a magnetic sector mass filter; (vii) a Time of Flight mass filter; and (viii) a Wein filter; and/or (k) a device or ion gate for pulsing ions; and/or (l) a device for converting a substantially continuous ion beam into a pulsed ion beam.

The mass spectrometer may further comprise either.

(i) a C-trap and an Orbitrap® mass analyser comprising an outer barrel-like electrode and a coaxial inner spindle-like electrode, wherein in a first mode of operation ions are transmitted to the C-trap and are then injected into the Orbitrap® mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the Orbitrap® mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The preferred embodiment is particularly advantageous in that the step of correcting the CCS calibration function during the course of an ion mobility experiment to correct for minor changes in one or more instrument parameters (e.g. temperature or pressure) enables very precise measurements of the collision cross section of analyte ions to be determined. As a result, detailed investigations of the conformational properties of e.g. peptides can be performed which were not previously possible.

It will be apparent, therefore, that the present invention represents a significant advance in the art in that it enables new detailed studies concerned with the conformational properties of peptides and other molecules to be performed.

BRIEF DESCRIPTION OF THE DRAWINGS

Various embodiments of the present invention will now be described, by way of example only, and with reference to the accompanying drawings in which:

FIG. 3 shows calculated collision cross section ("CCS") values for acetylated and non-acetylated RISELR and RLSELR peptides;

FIG. 9 shows calculated collision cross section ("CCS") values for acetylated and non-acetylated KISELR and KLSELR peptides;

FIG. 11 shows derived CCS values for acetylated and non-acetylated RISDLR, RLSDLR, KISDLR and KLSDLR peptides.

DETAILED DESCRIPTION OF THE PREFERRED EMBODIMENTS

A preferred embodiment of the present invention will now be described.

Figure 1:
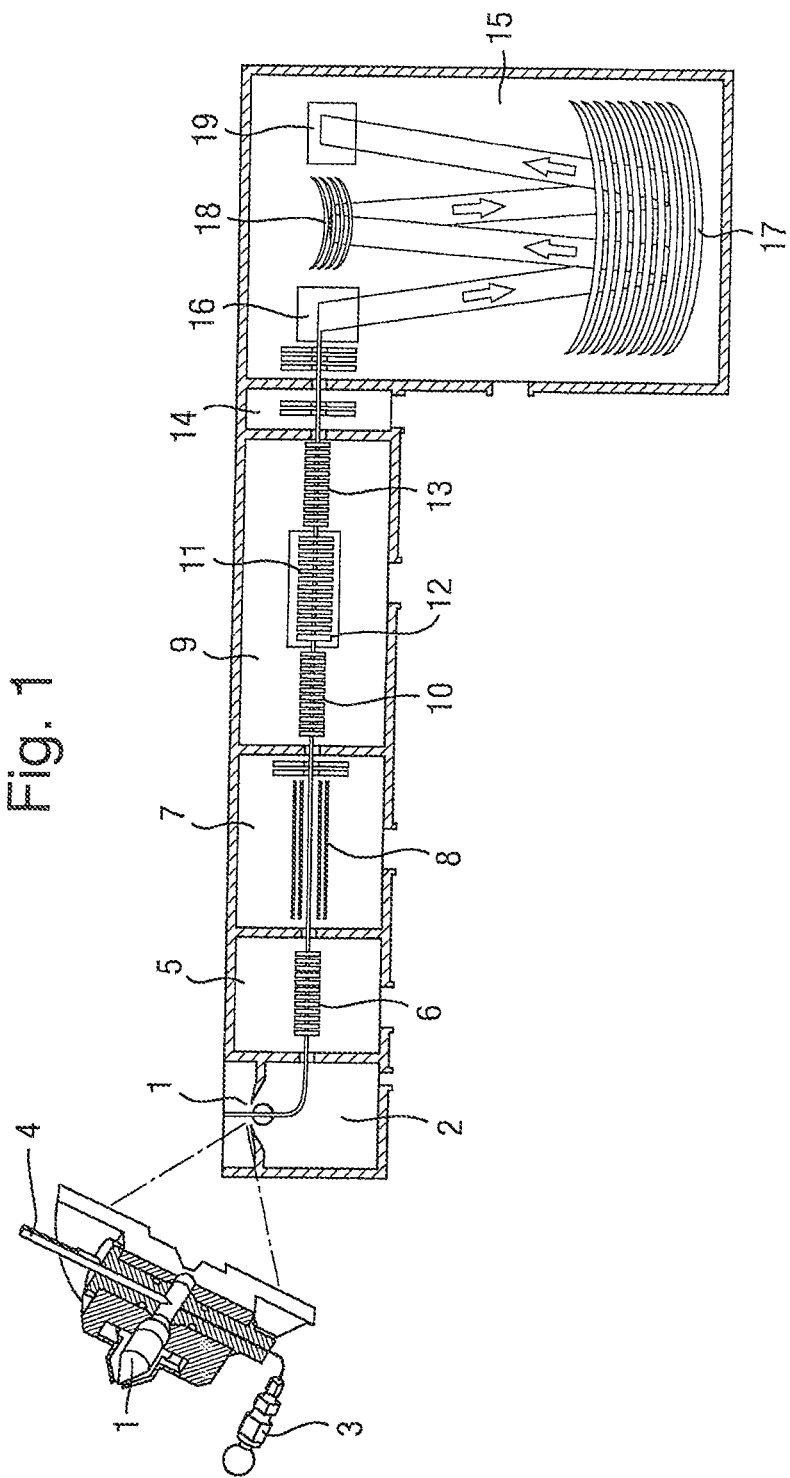
FIG. 1 shows a mass spectrometer incorporating an ETD fragmentation device according to an embodiment of the present invention.

Experiments were performed on a prototype Synapt G2® instrument (Waters Corp., Manchester, UK) fitted with a glow discharge source for anion generation as shown in FIG. 1. The mass spectrometer comprised a sampling cone 1 leading into a first vacuum chamber 2. In a mode of operation reagent gas (e.g. 1,3-dicyanobenzene) from a reagent gas supply device 3 was supplied adjacent a Glow Discharge ion source 4 comprising a discharge pin. The discharge pin was maintained at 500 V in order to ionise the reagent gas. The reagent gas was ionised by the Glow Discharge ion source 4 to form reagent ions which were then transferred to an ion trap 10 within a fourth vacuum chamber 9 of the mass spectrometer.

The mass spectrometer comprised a second vacuum chamber 5 housing an ion guide 6. One or more transient DC voltage potentials or voltages were applied to the electrodes of the ion guide 6 in order to cause a plurality of axial DC potential wells to be translated along the length of the ion guide 6 in order to urge ions along and through the ion guide 6. The ions then passed into a third vacuum chamber 7 which housed a quadrupole rod set 8. The quadrupole rod set 8 may be operated either as a mass filter or as an ion guide (in a non-mass selective mode of operation).

Ions which were onwardly transmitted by the quadrupole 8 then passed into the fourth vacuum chamber 9. The fourth vacuum chamber 9 housed an ion trap 10, an ion mobility spectrometer or separator 11 and a transfer Twave device 13. The ion mobility spectrometer or separator 11 comprised an optional helium cell 12 as an inlet stage. The helium cell 12 enabled ions to be driven into the relatively high pressure ion mobility spectrometer or separator 11 without the risk of the ions fragmenting.

According to an embodiment an Electrospray ion source (not shown) was switched ON during a first mode of operation which lasted approximately 1 s. During the first mode of operation analyte ions were generated by the Electrospray ion source and were transmitted to and trapped within the ion trap 10.

The Electrospray ion source was then switched OFF during a second mode of operation (or interscan period) which lasted approximately 0.1 s. When the Electrospray ion source was switched OFF during the second mode of operation, the Glow Discharge ion source 4 was switched ON. Reagent ions were generated by the Glow Discharge ion source 4 and were transmitted to and trapped within the ion trap 10. At the end of the second mode of operation the Glow Discharge ion source was switched OFF, the Electrospray ion source was switched ON and the cycle was repeated multiple times.

According to the preferred embodiment positively charged analyte ions and negatively charged reagent ions were generated at different times and were caused to be trapped together and interact via Electron Transfer Dissociation ("ETD") within the ion trap 10. As a result, the analyte ions were caused to fragment by exchanging charge with the reagent ions to form ETD product or fragment ions.

ETD product or fragment ions formed in the ion trap 10 were then transmitted to the ion mobility spectrometer or separator 11. Ions within the ion mobility spectrometer or separator were caused to become temporally separated as they passed through the ion mobility spectrometer or separator 11 and to separate according to their ion mobility.

ETD product or fragment ions which emerged from the ion mobility spectrometer or separator 12 may optionally be fragmented by Collision Induced Dissociation ("CID") by accelerating the ions into the transfer Twave device 13.

Ions which emerged from the transfer Twave device 13 were then passed through a short fifth vacuum chamber 14 housing a lens arrangement and then passed into a sixth vacuum chamber 15 housing a Time of Flight mass analyser. The Time of Flight mass analyser comprised a high field pusher 16, a dual stage reflectron 17, an ion mirror 18 and an ion detector system 19.

Figure 2:
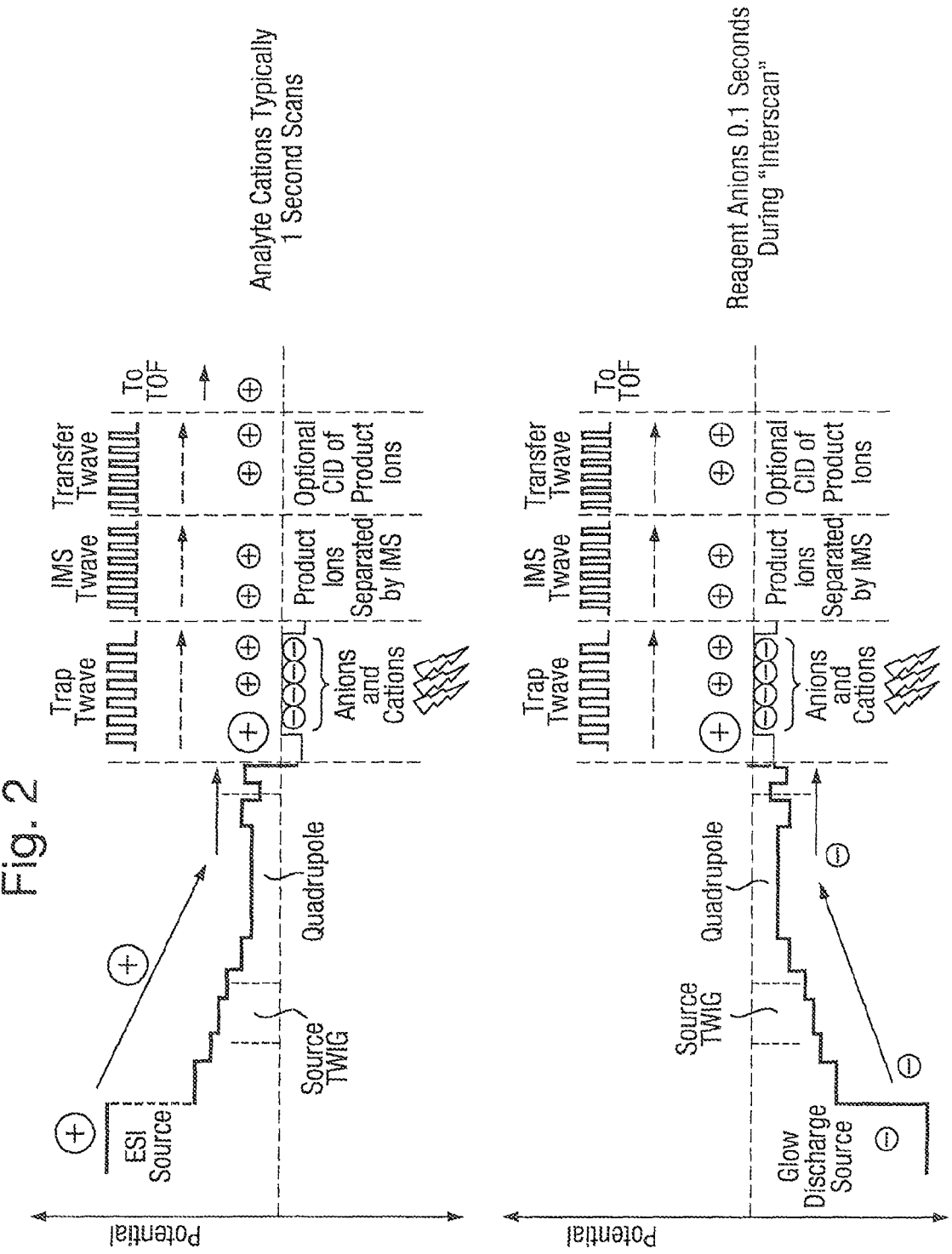
FIG. 2 shows a scanning sequence for injecting analyte cations and reagent anions into an ion trap so that the analyte ions interact with reagent ions by ETD according to an embodiment of the present invention.

FIG. 2 shows a scanning sequence relating to the injection of analyte cations and reagent anions into the ion trap 10 shown in FIG. 1 in accordance with an embodiment of the present invention. The mass spectrometer comprises an ESI ion source for analyte cation generation and a glow discharge source 4 for reagent anion generation. The analyte cations and reagent anions are each transmitted through the T-wave ion guide ("Source TWIG") 6 and the quadrupole rod set 8 before interacting via Electron Transfer Dissociation ("ETD") in the ion trap 10.

The T-wave ion guide 6 preferably comprises a plurality of electrodes each having an aperture through which ions are transmitted. Travelling or transient DC voltages or potentials are applied to the electrodes. One or more transient DC voltages or potentials or one or more transient DC voltage or potential waveforms are progressively applied to the electrodes of the ion guide 6 so that ions are urged along the length of the ion guide 6. In a similar manner, one or more transient DC voltages or potentials are also applied to the ion trap 10.

After the reagent anions and analyte cations have interacted in the ion trap 10, the resulting ETD product or fragment ions are then separated according to their ion mobility by a downstream IMS device 11. The ions are then transferred via a transfer Twave device 13 to a Time of Flight ("TOF") mass analyser. In the transfer Twave device 13 the product ions may optionally be subjected to Collision Induced Dissociation ("CID") or fragmentation.

One or more transient DC voltages or potentials or one or more transient DC voltage or potential waveforms are progressively applied to the electrodes of the ion mobility spectrometer or separator 11 and the transfer Twave device 13 so that ions are urged along the length of the ion mobility spectrometer or separator 11 and the transfer Twave device 13.

N-terminally acetylated and non-acetylated model peptides with R, H or K in the first position and E or D in the fourth position were obtained from The NEO Group (Cambridge, Mass.). Peptides having a 2+ charge state were selected using the quadrupole mass filter 8.

An initial CCS calibration was performed using polyalanine. Experimentally measured drift times were correlated with CCS values in a known Clemmer database. The absolute error with this method was regularly observed to be within 2% of the calculated cross section. As a result, an initial calibration function was generated which enabled an experimentally observed ion mobility drift time to be correlated with a corresponding collision cross section ("CCS") value.

According to the preferred embodiment experimentally derived CCS values of z-series ions were then used as an internal standard to ensure an accurate comparison between samples and to determine the level of significance. According to the preferred embodiment the initial calibration function was corrected or adjusted during the course of an experimental acquisition in order to enhance accuracy.

According to the preferred embodiment one or more known ion mobility peaks which are either introduced or which more preferably already exist within the acquired data are used to adjust the calibration function to correct for small but potentially significant changes in e.g. drift gas pressures or temperatures that may occur during the timescale of an experimental acquisition or a subsequent acquisition.

It is known to use multi-point external and internal calibration techniques to determine an (initial) calibration function. However, it is not known to then adjust or refine the calibration function during the course of an experimental acquisition based upon a single internal reference to correct for dynamic changes to gas pressures and temperatures.

The two known ways of generating an (initial) calibration function will firstly be discussed below before a single point internal lock-mobility correction technique according to a preferred embodiment of the present invention is discussed.

Multi-Point External Calibration

Multi-point external calibration is known and comprises acquiring ion mobility data for a known calibration standard containing multiple ion mobility peaks. The apex or peak centres of the ion mobility arrival time distributions or centred drift time for each peak (T) are then determined. A mathematical calibration function is then generated.

The mathematical calibration function which is generated comprises a plurality of known collision cross sections ("CCS") as a function of observed ion mobility drift time i.e. CCS (T).

According to the known technique the calibration function may be written in the form:

$$CCS = a + b.T + c.T^2 + d.T^3 \quad (1)$$

or alternatively in the form:

$$CCS = A + B.T^c \quad (2)$$

wherein a, b, c, d and A, B, C are constants which are experimentally determined from the acquired calibration data.

The terms in the calibration function include terms relating to mass, charge and other instrumental parameters such as temperature, pressure, polarisability of drift gas and the length of the drift cell or ion mobility spectrometer or separator.

According to the known technique an unknown sample is then acquired and the ion mobility drift time of the unknown sample is then determined. The calibration function is then applied to the unknown drift time peak in order to determine the collision cross section of the unknown sample.

As discussed above, the known multi-point external calibration approach is unable to correct for dynamic changes in instrument parameters such as small pressure and temperature changes which may occur during the timescale of an experimental acquisition.

Multi-Point Internal Calibration

A multi-point internal calibration technique is also known and comprises mixing a known calibrant standard with an unknown sample. Ion mobility data is then acquired and a peak list is generated in a similar manner to the known multi-point external calibration method described above.

A mathematical calibration function (i.e. known collision cross sections ("CCS") as a function of ion mobility drift times) is then generated. The mathematical calibration function can be represented as CCS (T).

The mathematical calibration function is then applied to the unknown drift time peak to determine its collision cross section.

Single Point Internal Lock-Mobility Correction

According to a preferred embodiment of the present invention a single point internal lock-mobility correction is preferably applied and utilised.

According to the preferred embodiment a multi-point calibration function may initially be determined and then may be applied initially to ion mobility data as described above in relation to the known multi-point external calibration.

However, once an initial calibration function has been generated then one or more known reference peaks present within the ion mobility data are preferably used to enhance or correct the initial calibration function during the current or subsequent experimental acquisitions.

The preferred embodiment is particularly advantageous compared with conventional techniques in that it is able to correct for small changes in experimental or instrumental parameters which may occur during the timescale of an experimental acquisition and hence enables some very detailed studies to be performed.

According to an embodiment lower order calibration constants and/or coefficients in an initial calibration function may be corrected or altered during the course of an experimental acquisition. For example, a constant a and/or a coefficient b in a calibration function similar to the one described above in relation to Eqn. 1 may be changed or otherwise altered during the course of an experimental acquisition. Similarly, the constant A in a calibration function similar to the one shown in Eqn. 2 above may be changed or otherwise altered.

Lower order calibration constants and/or coefficients are preferably changed or altered so that the one or more known lock-mobility drift time peaks preferably give the correct (or at least improved) CCS value.

The preferred method advantageously provides first order corrections for small changes in pressure, temperature, T-wave voltages etc. that may have occurred since the initial multi-point external calibration was applied.

According to the preferred embodiment only corrections of the low order constants and/or coefficients may be needed and the higher order calibration coefficients may preferably be left unchanged. However, less preferred embodiments are also contemplated wherein additionally and/or alternatively the higher order coefficients in the calibration function may be adjusted.

The correction to the calibration function may be performed either on the fly (i.e. on a spectrum by spectrum basis in real-time) or as part of a post processing technique.

The known calibration peaks which are preferably utilised to correct or revise the calibration function may comprise one or more parent or precursor ions in an MS/MS experiment. Additionally and/or alternatively, the known calibration peaks may comprise one or more known fragment or product ions.

The advantage of the method according to the preferred embodiment over e.g. the known multi-point internal calibration method is that only one single known calibrant point is required. However, a second order correction may also be utilised wherein two or more lock-mobility peaks are considered.

Some examples of experimental data which have been obtained using corrected collision cross sections according to an embodiment of the present invention will now be presented. The experimental results demonstrate how the preferred embodiment enables some very detailed Investigations into the conformational properties of ions to be performed. Such detailed investigations would not otherwise be possible.

It will be apparent, therefore, that the preferred embodiment enables a significant Improvement in accuracy to be achieved.

FIG. 3 shows some experimentally derived or determined results of CCS values for acetylated and non-acetylated RLSELR and RISELR peptides using the improved calibration correction method of the preferred embodiment.

Figure 4A:
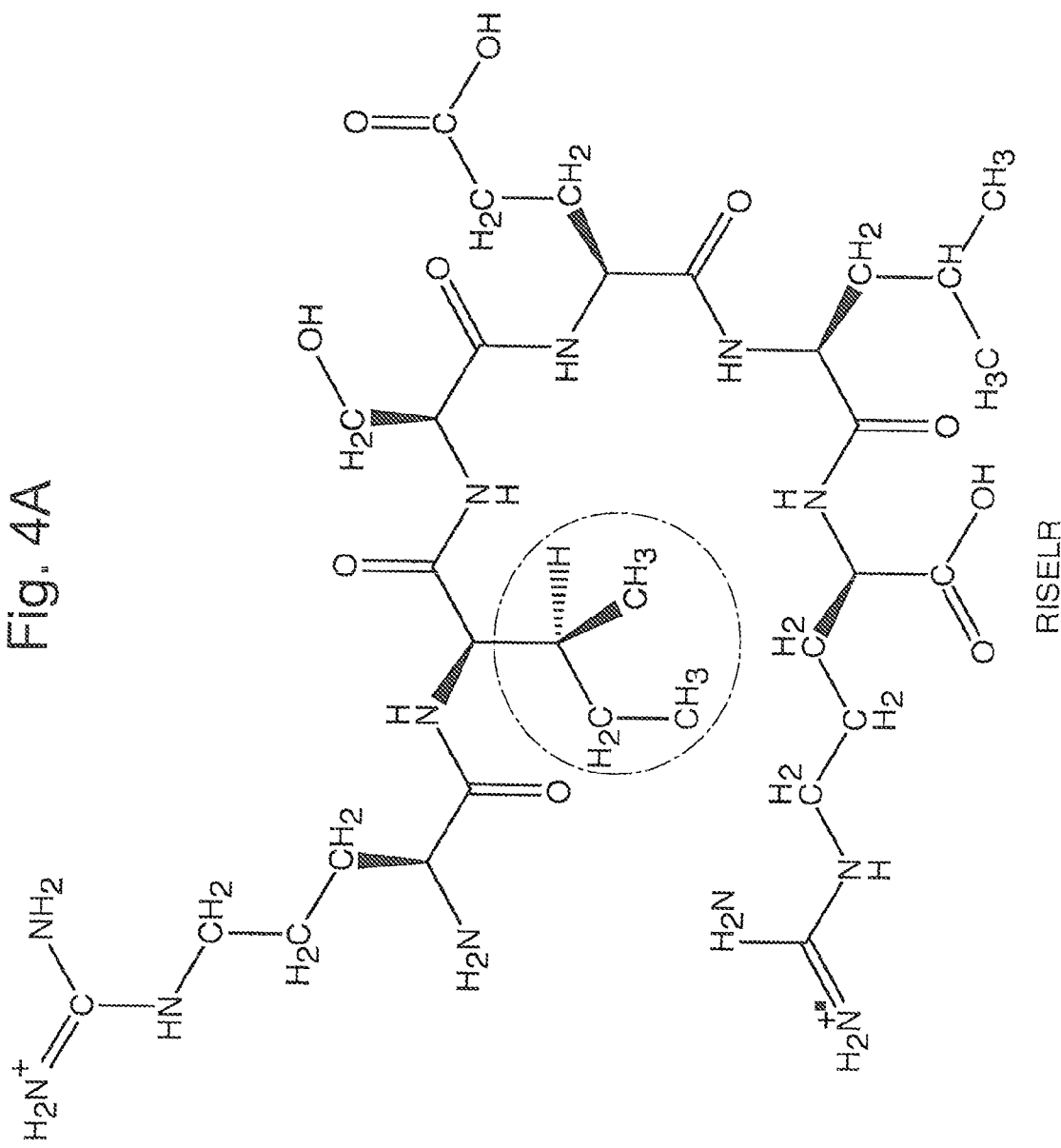
FIG. 4A shows a proposed molecular ion conformation of a radical cation of a non-acetylated RISELR peptide based upon ion mobility experiments and FIG. 4B shows a proposed molecular ion conformation of a radical cation of a non-acetylated RLSELR peptide based upon ion mobility experiments.
Figure 4B:
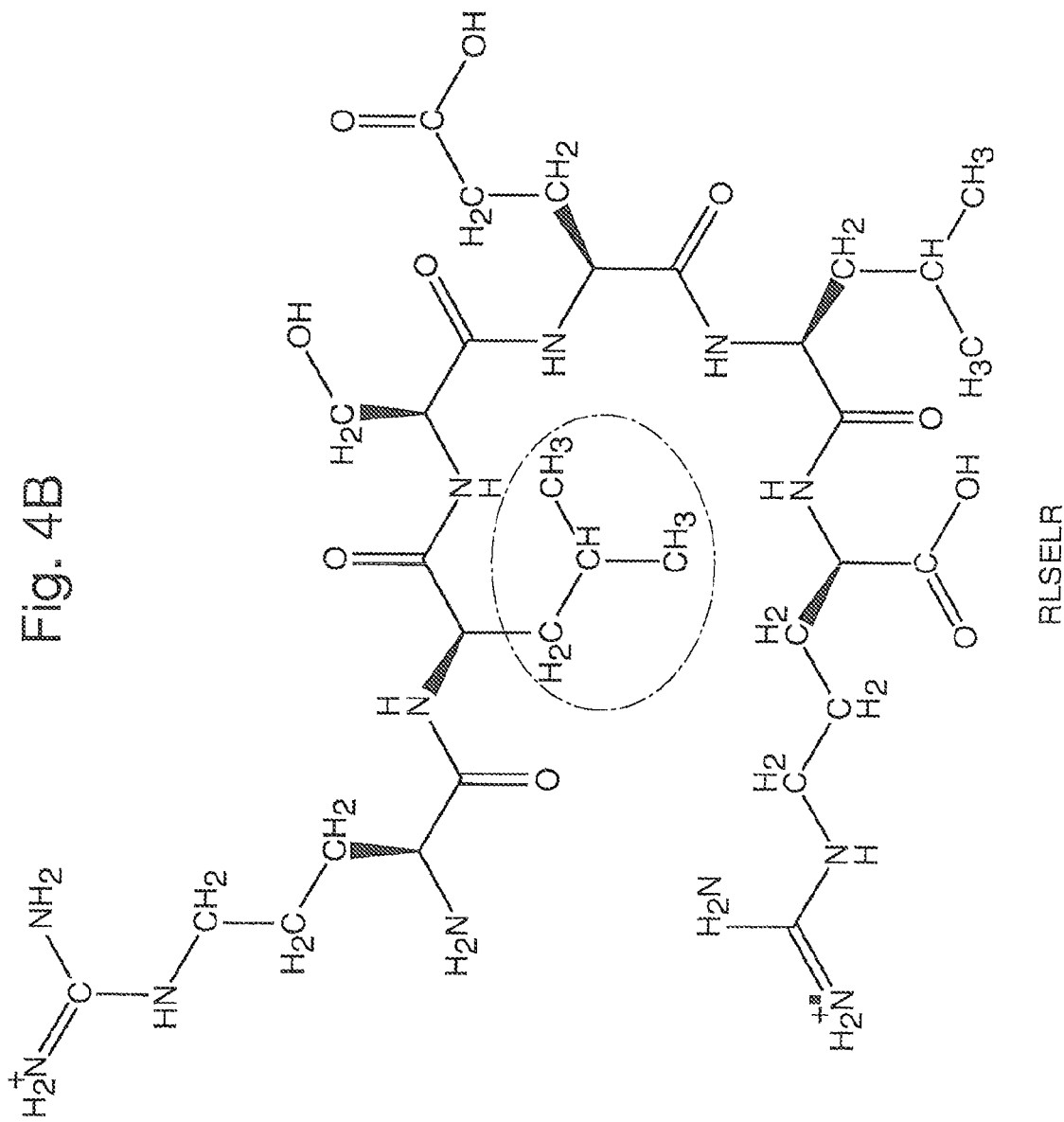

On the basis of the accurately determined CCS values some detailed molecular ion conformations can be proposed. FIGS. 4A and 4B show proposed molecular ion conformations for radical cations of non-acetylated RISELR and RLSELR peptides based upon ion mobility experiments performed in accordance with the preferred embodiment.

Figure 5A:
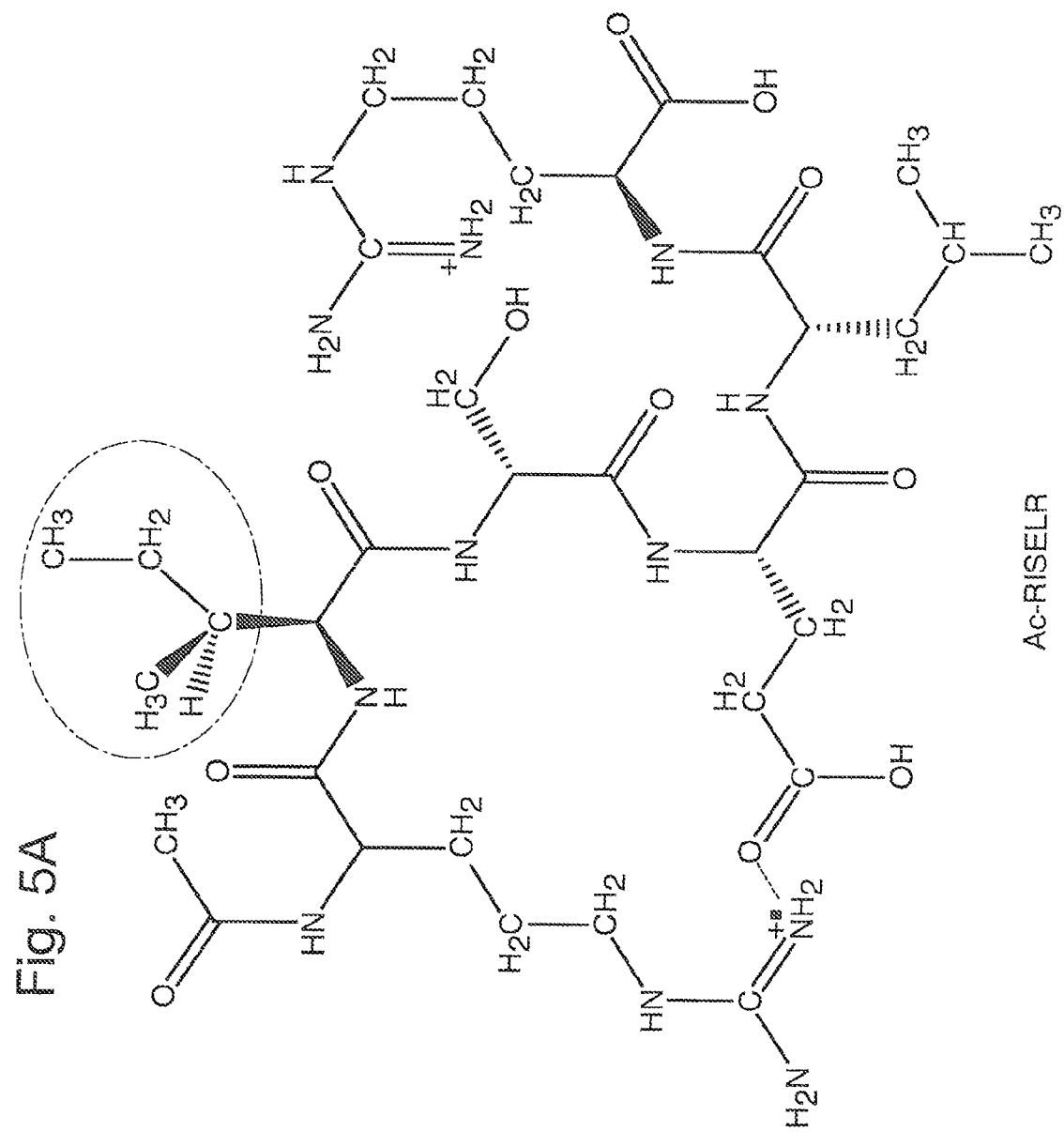
FIG. 5A shows a proposed molecular ion conformation of a radical cation of an acetylated RISELR peptide based upon ion mobility experiments and FIG. 5B shows a proposed molecular ion conformation of a radical cation of an acetylated RLSELR peptide based upon ion mobility experiments.
Figure 5B:
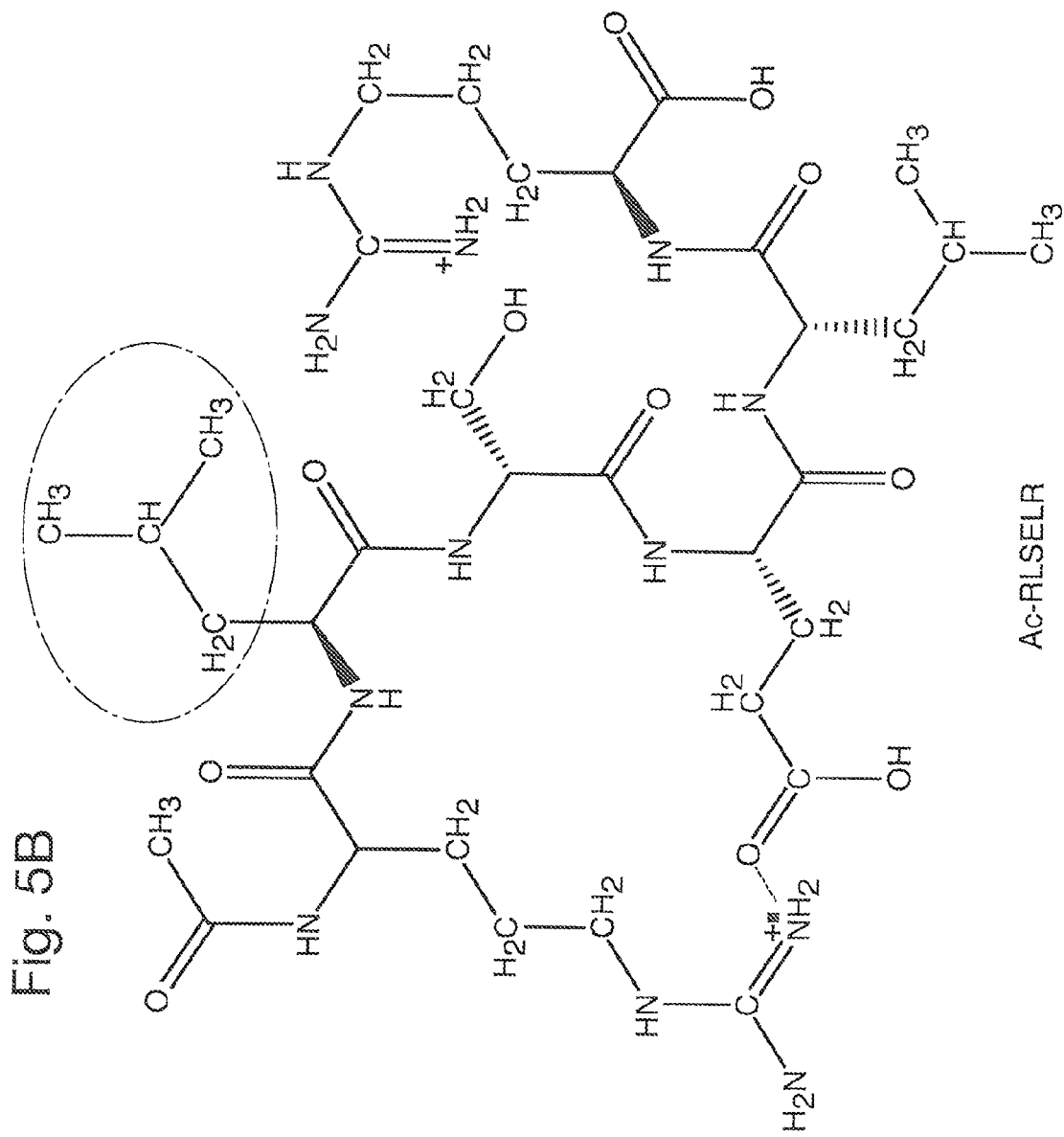

FIGS. 5A and 5B show proposed molecular ion conformations for a radical cation of acetylated RISELR and RLSELR peptides based on ion mobility experiments performed according to the preferred embodiment.

It has been previously determined that the CCS of isoleucine (I) is smaller than that of leucine (L). However, as is apparent from FIG. 3 (see shaded boxes for c4 and c5 ions for RISELR) the experimentally determined CCS values of the c4 and c5 ions does not follow the expected I<L trend since the experimentally determined CCS values for RISELR are greater than those for RLSELR.

Similarity of the $[M+2H]^{+-}$ and $[M+H]^+$ CCS values between the I and L containing peptides as shown in FIG. 3 suggests that the side-chains of these residues are buried in the structure.

With reference again to the FIG. 3, the small change in CCS value between the $[M+2H]^{+-}$ and $[M+H]^+$ species suggests that the loss of $H^-$ does not disrupt any salt bridges in the proposed structures. As a result, minimal conformation changes are observed.

It has been found that acetylation of the N terminus changes the peptide structure significantly and that loss of $H^-$ causes significant conformation change between $[M+2H]^{+-}$ and $[M+H]^+$. FIG. 3 also shows experimentally determined CCS values for acetylated and non-acetylated c-ions for both RISELR and RLSELR.

Figures 6, 7:
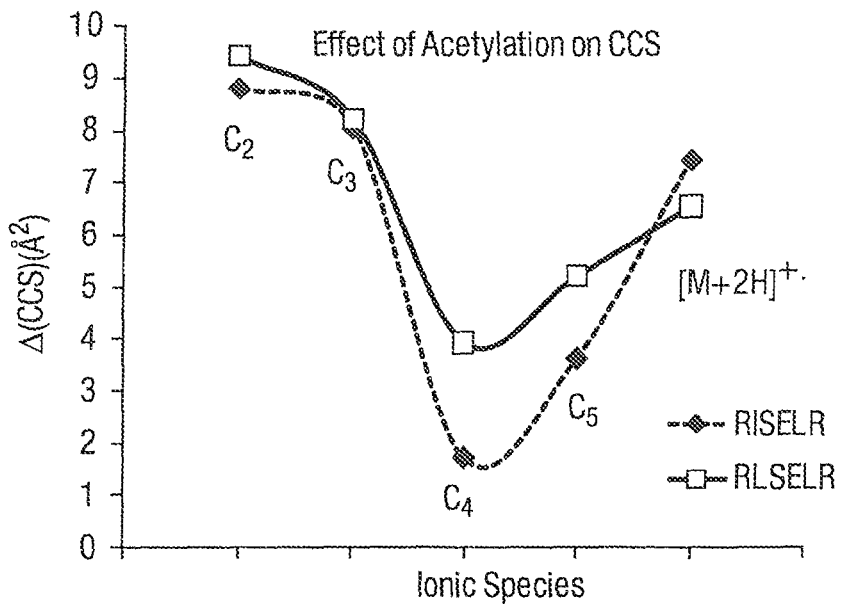
FIG. 6 shows the effect of acetylation on collision cross section and in particular shows the difference in measured CCS values between acetylated and non-acetylated c-ions for RISELR and RLSELR peptides.
FIG. 7 shows derived CCS values for acetylated and non-acetylated HISELR and HLSELR peptides.

FIG. 6 shows the difference in the measured CCS values between acetylated and non-acetylated c-ions for both RISELR and RLSELR. The CCS trend of the c-ions for acetylated and non-acetylated peptides as shown in FIG. 6 suggests a conformation contraction when acidic amino acid is present in the fragment. The relative CCSs of fragments containing I are smaller than those with L. The sidechain of these residues is probably more exposed in this case.

Experimentally derived CCS values for acetylated and non-acetylated HISELR and HLSELR peptides are shown in FIG. 7. The c-series reflects the difference in CCS of I and L as expected. The calculated CCSs of $[M+2H]^{+-}$ and $[M+2H]^{+-}$ for these peptides shows that loss of $H^-$ causes little or no conformation change.

Figure 8A:
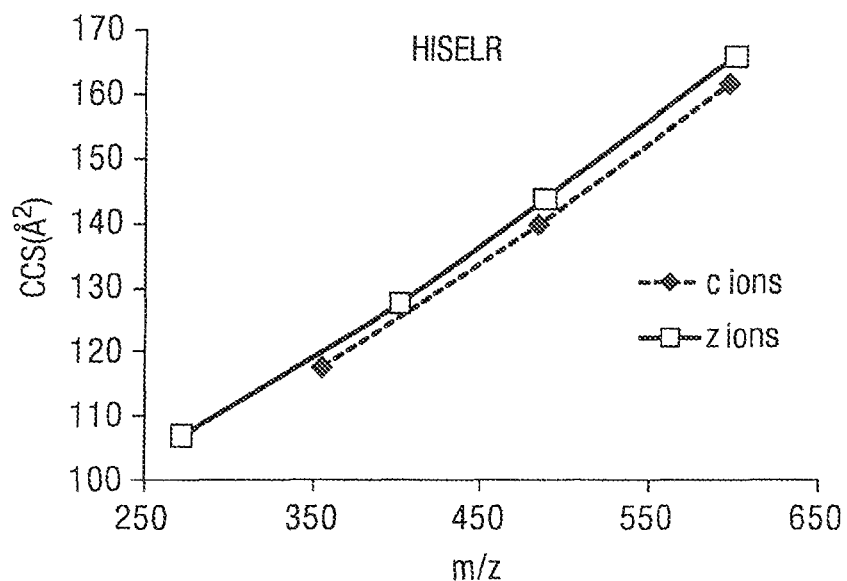
FIGS. 8A and 8B illustrates how the CCS value increases with increasing fragment ion size for HISELR and HLSELR peptides.
Figure 8B:
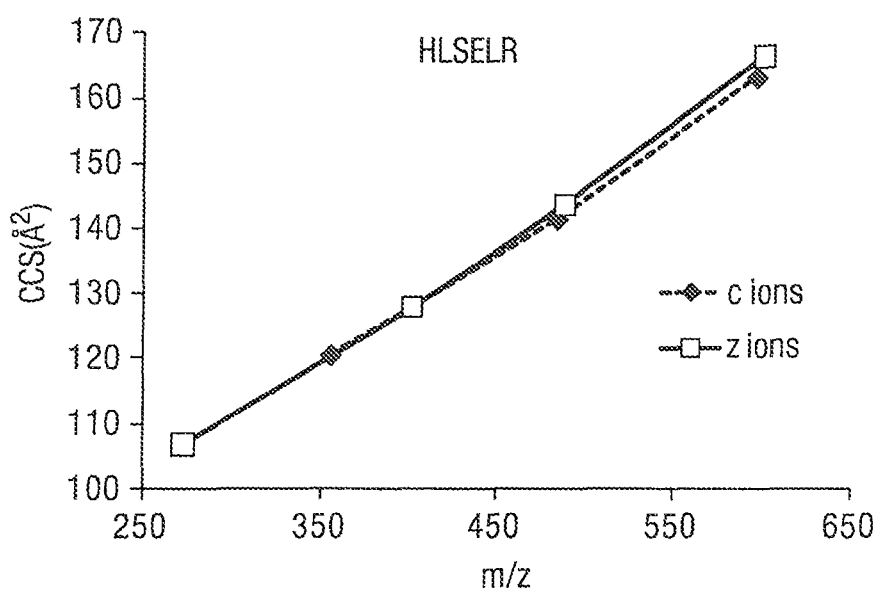

FIGS. 8A and 8B shows how the CCS of c- and z-fragment ions increases linearly with size for both HISELR and HLSELR peptides.

The absence of a conformation collapse may be attributed to a lack of side chain interactions.

Figure 10:
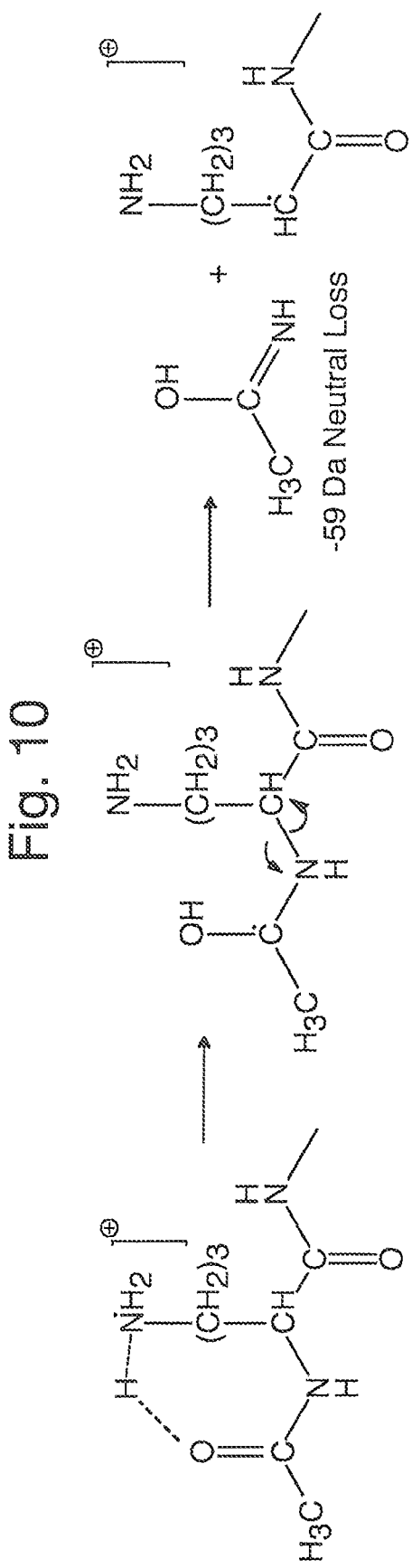
FIG. 10 shows a radical driven loss of a N-terminal Ac group.

Experimentally derived CCS values for acetylated and non-acetylated KLSELR and KISELR peptides are shown in FIG. 9. The fragmentation of K-containing peptides shows similar trends to those observed with H. A relatively large $Ac^-$ loss (−59 Da) from the $[M+2H]^+$ ion was observed for these peptides. This loss is presumed to be due to a radical-driven cleavage of the N—C bond as shown in FIG. 10. This neutral loss may be kinetically favoured explaining the absence of c-series fragment ions.

Experimentally derived CCS values for acetylated and non-acetylated RLSELR, RISELR, KISDLR and KLSDLR are shown in FIG. 11. R and K containing peptides show similar behaviours when D is present. Loss of H from $[M+2H]^{+-}$ results in a conformation change for all analogs, suggesting the presence of an interaction between basic and acidic side chains.

Ion mobility measurements of ETD fragment ions as performed according to embodiments of the present invention can provide detailed insight for explaining presence or absence of fragment ions in a mass spectrum. For example, the CCS difference between charge reduced and ETnoD ions can be a useful indicator for the structure of the radical cation.

Although the present invention has been described with reference to preferred embodiments, it will be understood by those skilled in the art that various changes in form and detail may be made without departing from the scope of the invention as set forth in the accompanying claims.

The invention claimed is:

1. A method of mass spectrometry comprising:
   separating a first plurality of ions including one or more known or reference ions according to their ion mobility and acquiring first ion mobility data;
   applying an initial calibration function to said first ion mobility data;
   determining an estimated property of said one or more known or reference ions;
   comparing said estimated property with a known property of said one or more known or reference ions; and
   varying said initial calibration function to generate a revised calibration function;
   wherein the step of varying said initial calibration function comprises altering one or more constants or one or more coefficients or one or more terms of said initial calibration function to generate said revised calibration function;
   wherein the step of varying said initial calibration function is performed in real-time during an experimental acquisition; and
   wherein the step of varying said initial calibration function comprises either: (a) altering a first order coefficient or a first order term in said initial calibration function; or (b) altering a second or higher order coefficient or a second or higher order term in said initial calibration function.

2. A method as claimed in claim 1, further comprising determining said initial calibration function using a multi-point external calibration method.

3. A method as claimed in claim 1, further comprising determining said initial calibration function using a multi-point internal calibration method.

4. A method as claimed in claim 1, wherein said initial calibration function relates experimentally determined ion mobility drift times of ions with a physico-chemical property of said ions.

5. A method as claimed in claim 4, wherein said physico-chemical property comprises a conformational property of said ions.

6. A method as claimed in claim 5, wherein said conformational property comprises a collision cross section ("CCS") of said ions.

7. A method as claimed in claim 1, wherein said estimated property or said known property comprises a collision cross section ("CSS") of said ions.

8. A method as claimed in claim 1, wherein an estimated property of said one or more known or reference ions as determined using said revised calibration function corresponds more closely with said known property of said one or more known or reference ions than an estimated property of said one or more known or reference ions as determined using said initial calibration function.

9. A method as claimed in claim 1, further comprising:
   separating a second plurality of ions according to their ion mobility and acquiring second ion mobility data;
   applying said revised calibration function to said second ion mobility data; and
   determining said estimated property of said second plurality of ions.

10. A method as claimed in claim 1, wherein said one or more known or reference ions comprise one or more parent or precursor ions.

11. A method as claimed in claim 1, wherein said one or more known or reference ions comprise one or more fragment, daughter or product ions.

12. A mass spectrometer comprising:
   an ion mobility spectrometer or separator arranged and adapted to separate a first plurality of ions including one or more known or reference ions according to their ion mobility; and
   a control system arranged and adapted:
   (i) to acquire first ion mobility data;
   (ii) to apply an initial calibration function to said first ion mobility data;
   (iii) to determine an estimated property of said one or more known or reference ions;

(iv) to compare said estimated property with a known property of said one or more known or reference ions; and (v) to vary said initial calibration function to generate a revised calibration function;

wherein said varying comprises altering one or more constants or one or more coefficients or one or more terms of said initial calibration function to generate said revised calibration function, and is performed in real-time during an experimental acquisition; and wherein the step of varying said initial calibration function comprises either: (a) altering a first order coefficient or a first order term in said initial calibration function; or (b) altering a second or higher order coefficient or a second or higher order term in said initial calibration function.

* * * * *